US00PP36197P3

(12) United States Plant Patent
Boches

(10) Patent No.: US PP36,197 P3
(45) Date of Patent: Oct. 15, 2024

(54) ***VACCINIUM* PLANT NAMED 'FC13-044'**

(50) Latin Name: *Vaccinium corymbosum*
Varietal Denomination: FC13-044

(71) Applicant: The Conard Pyle Company, West Grove, PA (US)

(72) Inventor: Peter Stefan Boches, Hilo, HI (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/103,730

(22) Filed: Jan. 31, 2023

(65) Prior Publication Data

US 2024/0260492 P1 Aug. 1, 2024

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC . A01H 5/08; A01H 5/00; A01H 6/368; A01H 6/36
See application file for complete search history.

(56) References Cited

U.S. PATENT DOCUMENTS

PP25,467 P3 4/2015 Brazelton et al.

*Primary Examiner* — June Hwu
(74) *Attorney, Agent, or Firm* — Panitch Schwarze Belisario & Nadel LLP; Stephany G. Small; Travis W. Bliss

(57) ABSTRACT

The new *Vaccinium* plant variety 'FC13-044' is provided. 'FC13-044' is a commercial variety. The variety is produced from a cross of 'FL04-245' (female parent, unpatented) and 'ZF09-233' (male parent, unpatented). The new variety produces white colored inflorescences. A medium green colored foliage is displayed. A moderately vigorous, compact, and very dense growth habit is exhibited.

3 Drawing Sheets

Latin name of the genus and species:
Genus—*Vaccinium.*
Species—*corymbosum.*
Variety denomination: The new blueberry plant claimed is of the variety denominated 'FC13-044'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of *Vaccinium* (*Vaccinium corymbosum*) plant, referred to as 'FC13-044', as herein described and illustrated.

The new cultivar originated in a controlled breeding program in Lowell, Oregon during Spring 2010. The objective of the breeding program was the development of superior *Vaccinium* cultivars that meet the evolving needs of the blueberry and home enthusiast industries.

The new *Vaccinium* cultivar is the result of cross-pollination. The female (seed) parent of the new cultivar is 'FL04-245', a non-introduced, non-patented breeder seedling. The male (pollen) parent of the new cultivar is 'ZF09-233', a non-introduced, non-patented breeder seedling. The seeds resulting for the above cross were sown and small plants were obtained which were physically and biologically different from each other. Selective study during Summer 2013 in a controlled environment at Lowell, Oregon, U.S.A. resulted in the identification of a single flowering plant of the new variety.

'FC13-044' has been found to undergo asexual propagation by softwood cuttings and in vitro propagules since Summer 2013 in Lowell, Oregon. Asexual propagation techniques in Lowell, Oregon, such as softwood cuttings and in vitro cultures, have shown that the characteristics of the new variety are homogenous, stable, and strictly transmissible by such asexual propagation from one generation to another. Accordingly, the new variety undergoes asexual propagation in a true-to-type manner with all the characteristics, as herein described, firmly fixed and retained through successive generations of such asexual reproduction.

SUMMARY OF THE INVENTION

The following characteristics of the new cultivar 'FC13-044' have been repeatedly observed and are determined to be the unique characteristics of the new *Vaccinium* plant:

1) White colored inflorescences,
2) Medium green colored foliage,
3) A moderately vigorous, compact, and very dense growth habit.

The new variety of the present invention can readily be distinguished from its ancestors. In particular, the 'ZF09-

233' variety (i.e., the pollen parent) has a less dense canopy and less uniform growth compared to the new cultivar. The 'FL04-245' variety (i.e., the seed parent) is no longer available for comparison. Moreover, the new variety can be readily distinguished from other similar non-parental varieties. For example, 'ZF08-095' (U.S. Plant Pat. No. 25,467) is the most similar commercially available *Vaccinium* cultivar in comparison to the new variety. Plants of the new cultivar produce 1-2 seeds per berry as compared to plants of 'ZF08-095', which produce 14 seeds per berry.

BRIEF DESCRIPTION OF THE DRAWINGS

The accompanying photographic illustration shows typical specimens in full color of the new variety 'FC13-044'. The colors are as nearly true as is reasonably possible in a color representation of this type. The color values cited in the detailed botanical description accurately describe the colors of the new blueberry. The illustrated *Vaccinium* plants of the new variety were approximately one year of age and were grown in Cochranville, Pennsylvania in August 2022.

DETAILED BOTANICAL DESCRIPTION

Figure 1:
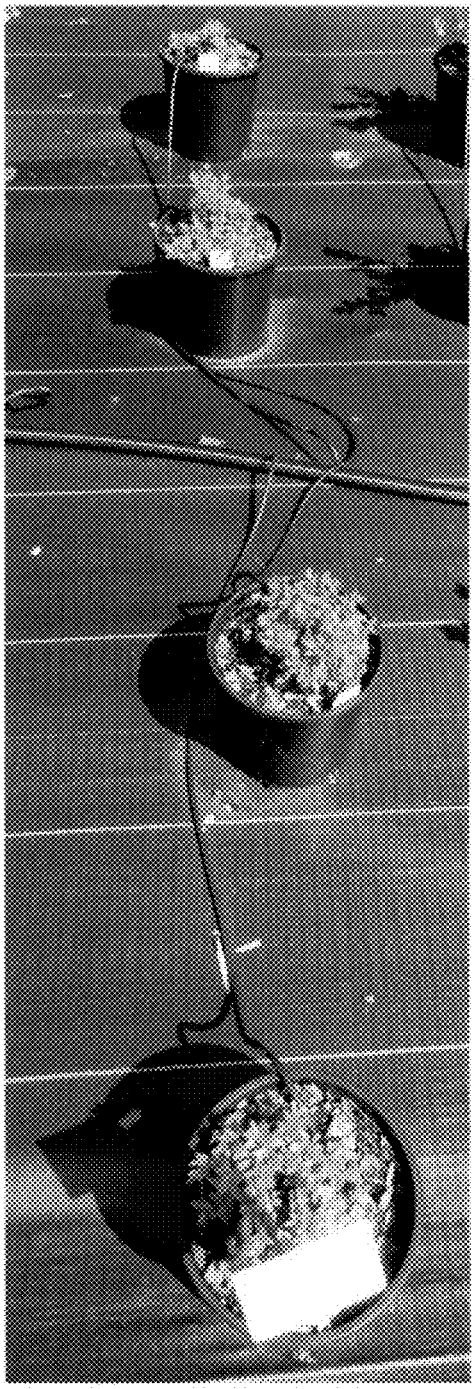
FIG. 1—illustrates container grown plants of 'FC13-044'
Figure 2:
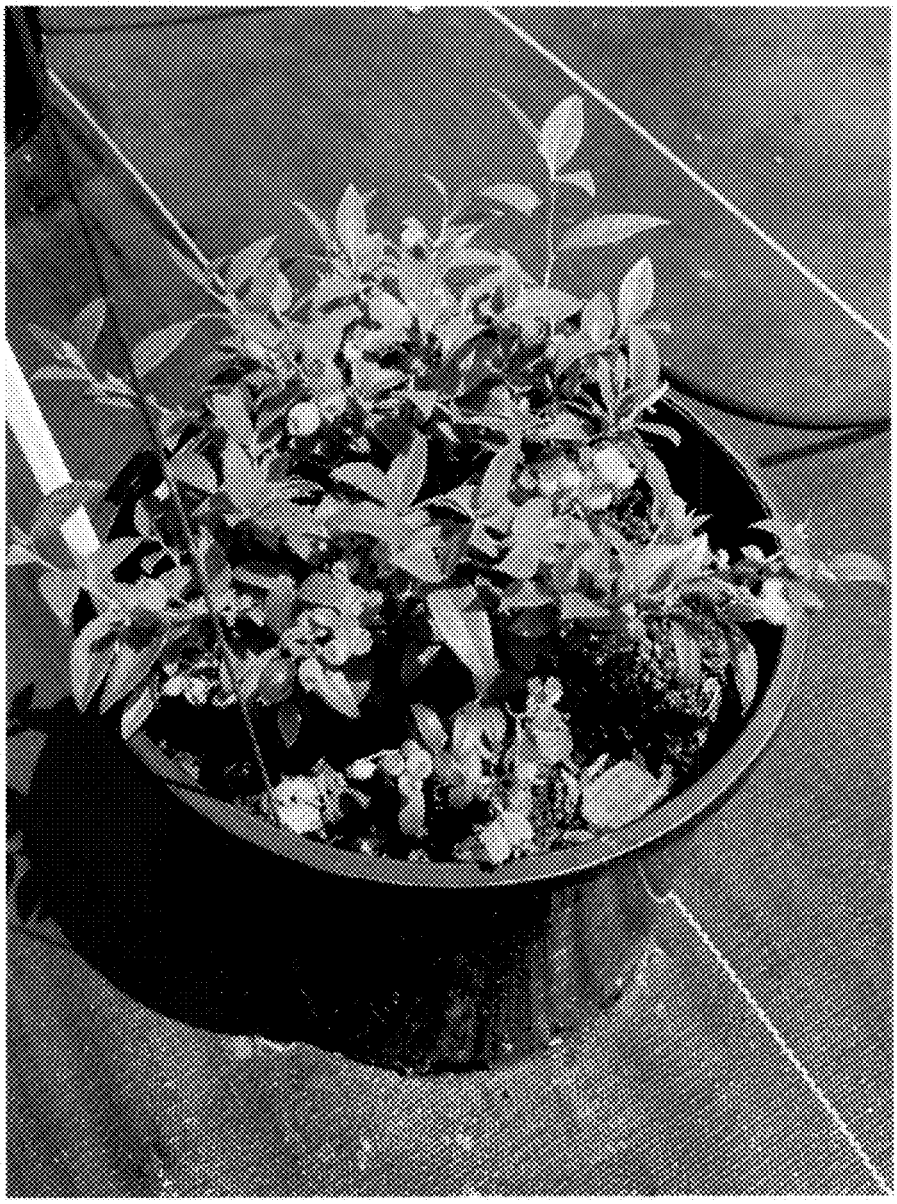
FIG. 2—illustrates plant of 'FC13-044' displaying overall growth habit
Figure 3:
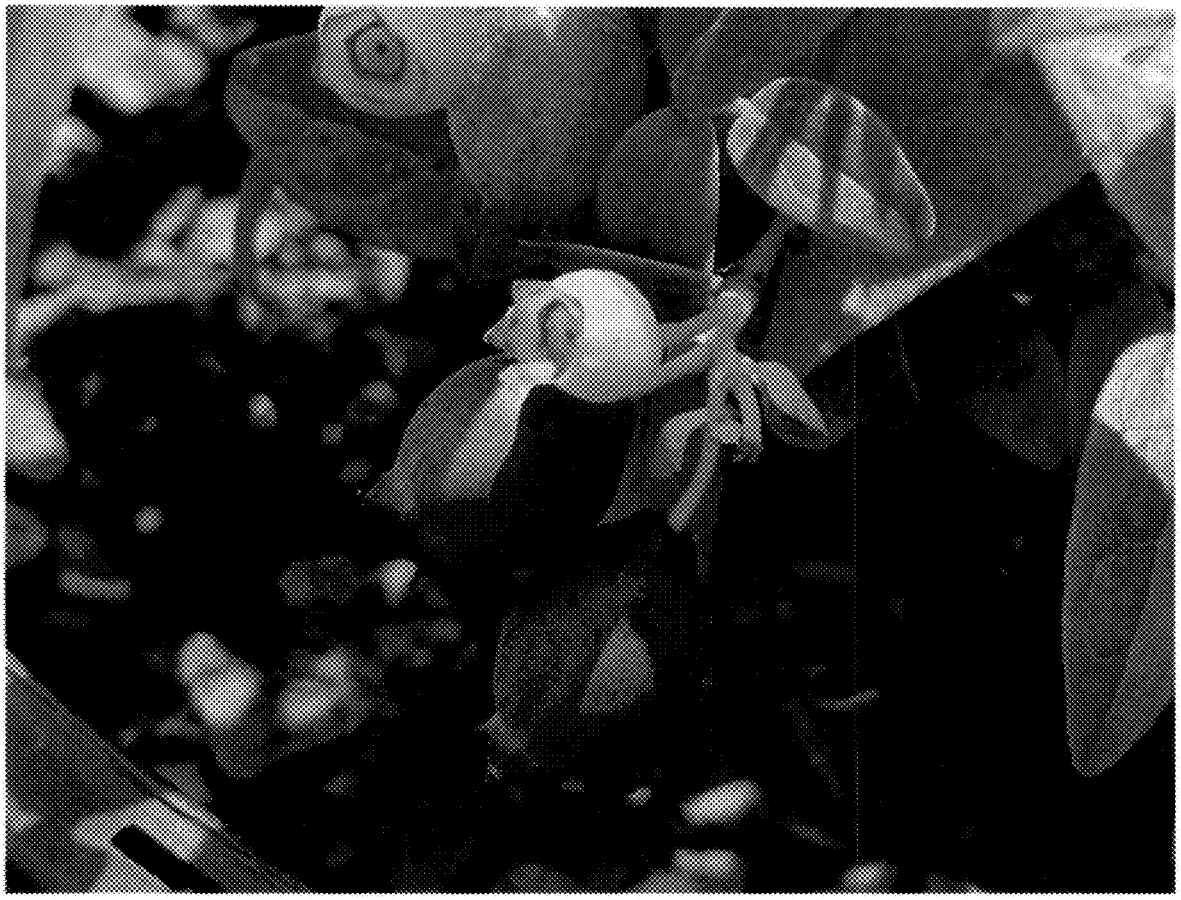
FIG. 3—illustrates a close-up view of developing fruit of 'FC13-044'

The following detailed description sets forth the distinctive characteristics of 'FC13-044'. The data which defines these characteristics was collected from asexual reproductions of the original selection. Dimensions, sizes, colors, and other characteristics are approximations and averages of typical plants of two years of age set forth as accurately as possible. The chart used in the identification of colors described herein is The R.H.S. Colour Chart of The Royal Horticultural Society, London, England, 2015 edition, except where general color terms of ordinary significance are used. The R.H.S. Colour Chart designation used herein represents the closest color observed on the majority of the specified botanical feature. The color values were determined under natural light conditions in Cochranville, Pennsylvania and represent the closest color observed on the majority of the specified botanical feature.

The new blueberry plant variety 'FC13-044' has not been observed under all possible environmental conditions. The phenotype may vary somewhat with variations in environment and cultural practices such as temperature and light intensity without, however, any variance in genotype.

GENERAL

Classification:

*Family*.—Ericaceae.

*Genus*.—*Vaccinium*.

*Species*.—*Corymbosum*.

Parentage:

*Female parent*.—'FL04-245' (unpatented).

*Male parent*.—'ZF09-233' (unpatented).

Plant description:

*Commercial crop time*.—Approximately one year from a rooted cutting to finish in a one-gallon container.

*Growth habit and general appearance*.—Moderately vigorous, compact, and dense growth habit.

*Hardiness*.—USDA Zone 5.

*Size*.—Height from soil level to top of plant plane: Approximately 13.0 cm. Width: Approximately 23.0 cm.

*Branching habit*.—Freely branching. Pinching enhances branching. Quantity of lateral branches per plant: Approximately 4 main branches.

*Branch*.—Strength: Strong. Length: Approximately 6.0 cm on average. Diameter: Approximately 3.0 mm. Length of central internode: Approximately 5.0 mm. Texture: Mostly smooth with some rough areas where the wood is starting to become harder. Color of mature stems: Yellow-Green Group 146B with some coloring of Greyed-Orange Group 177B and 177A where the wood is starting to become harder.

Foliage description:

*General description*.—Fragrance: None detected. Form: Simple. Arrangement: Alternate. Time of beginning vegetative growth: Early to mid-spring.

*Leaves*.—Shape: Elliptic. Margin: Entire. Apex: Acute. Base: Cuneate. Venation pattern: Pinnate. Length of mature leaf: Approximately 3.0 cm. Width of mature leaf: Approximately 1.3 cm. Texture of upper and lower surfaces: Glabrous and glossy. Color of upper and under surfaces of young foliage: Green Group 143C with indistinguishable venation. Color of upper surface of mature foliage: Green Group 137A with indistinguishable venation. Color of lower surface of mature foliage: Green Group 137C with indistinguishable venation.

*Petiole*.—Length: Approximately 2.0 mm. Diameter: Approximately 1.0 mm. Texture: Glabrous. Color: Yellow-Green Group 144B.

Flowering description:

*Flowering season*.—Flowers in early spring in southeastern Pennsylvania.

*Lastingness of individual inflorescence on the plant*.—Approximately one week.

Flower description:

*General description*.—Shape: Urceolate. Quantity per plant: Approximately 100 fully open on a plant at a given time. Quantity per cluster: Approximately 6 flowers per cluster. Fragrance: Very slight, sweet. Aspect: Pendulous.

*Bud just before opening*.—Shape: Oval. Length: Approximately 1.1 cm. Diameter: Approximately 0.5 cm. Color: Green-White Group 157D.

*Corolla*.—Color: White Group 155A. Length: Approximately 1.0 cm. Width: Approximately 5.0 mm. Aperture width: Approximately 4.0 mm.

*Calyx*.—Shape: Star-shaped. Depth: Approximately 4.0 mm. Diameter: Approximately 6.0 mm.

*Sepals*.—Quantity: 5. Shape: Ovate. Margin: Entire. Apex: Acute. Base: Fused. Length: Approximately 4.0 mm. Width: Approximately 2.0 mm. Texture of upper surface: Glabrous. Texture of lower surface: Glabrous. Color of upper and lower surfaces: Green Group 143B.

*Peduncle*.—Length: Approximately 7.0 mm. Surface Texture: Unarmed and smooth. Color: Green Group 138A.

*Pedicel*.—Length: Approximately 4.0 mm. Surface Texture: Unarmed and smooth. Color: Green Group 143C.

*Reproductive organs*.—Androecium: Stamen quantity per flower: Approximately 10. Stamen length:

Approximately 3.0 mm. Anther shape: Narrow oblong. Anther length: Approximately 1.0 mm. Anther color: Greyed-Orange Group N167A. Pollen amount: Not observed. Gynoecium: Pistil quantity: 1 per flower. Pistil length: Approximately 1.2 cm. Stigma shape: Flat Disc. Stigma color: Yellow-Green Group 145A. Style length: Approximately 1.0 mm. Style color: Yellow-Green Group 145B. Ovary length: Approximately 2.0 mm. Ovary color: Yellow-Green Group 146C.

Fruit description:

*Date of* 50% *maturity*.—Late June to early July in Southeastern Pennsylvania.

*Fruit development period*.—80 to 85 days. Fruiting on one-year old shoots, not found on current season wood in most circumstances.

*Developing berry color*.—Black Group 202A.

*Ripe berry color*.—Greyed-Purple Group N186A.

*Berry surface wax abundance*.—Low.

*Fruit bloom intensity*.—Weak.

*Berry flesh color*.—Greyed-Green Group 198B.

*Berry size*.—Height from calyx to scar: 1.0 cm. Diameter: 8.0 mm. Diameter of the fruit calyx basin: 1.7 mm. Depth of the fruit calyx basin: 0.7 mm.

*Berry shape*.—Oval.

*Berry firmness*.—Soft.

*Berry flavor and texture*.—Tart flavor, soft texture. Medium amount of berry sweetness and acidity.

*Suitability of mechanical harvesting*.—Not suitable.

*Uses*.—Intended for home gardens, container gardening, and/or ornamental uses.

Seed description:

*Seed abundance in fruit*.—Very low, with approximately 1 to 2 seeds per berry.

*Seed color*.—200B.

*Seed size*.—1.0 mm long; 1.0 mm wide.

Disease and pest resistance: Resistance to pathogens and pests common to *Vaccinium* has not been observed.

The invention claimed is:

1. A new and distinct variety of blueberry plant named 'FC13-044', substantially as illustrated and described herein.

* * * * *